(12) United States Patent
Kutscher et al.

(10) Patent No.: US 7,847,929 B2
(45) Date of Patent: Dec. 7, 2010

(54) METHODS AND APPARATUS FOR INSPECTING A PLURALITY OF DIES

(75) Inventors: Tuvia Dror Kutscher, Shoham (IL); Zvi Goren, Ness-Tziona (IL); Efrat Rozenman, Asseret (IL); Rami Elichai, Asqelon (IL)

(73) Assignee: Applied Materials Israel, Ltd., Rehovot (IL)

( * ) Notice: Subject to any disclaimer, the term of this patent is extended or adjusted under 35 U.S.C. 154(b) by 397 days.

(21) Appl. No.: 11/466,583

(22) Filed: Aug. 23, 2006

(65) Prior Publication Data

US 2008/0259326 A1 Oct. 23, 2008

(51) Int. Cl.
G01N 21/00 (2006.01)

(52) U.S. Cl. ................... 356/237.5; 356/237.2

(58) Field of Classification Search .... 356/237.4–237.5
See application file for complete search history.

(56) References Cited

U.S. PATENT DOCUMENTS

| | | | |
|---|---|---|---|
| 5,173,719 A * | 12/1992 | Taniguchi et al. | 356/394 |
| 5,825,482 A | 10/1998 | Nikoonahad et al. | |
| 6,407,809 B1 * | 6/2002 | Finarov et al. | 356/237.3 |
| 6,809,808 B2 | 10/2004 | Feldman et al. | |
| 6,853,475 B2 | 2/2005 | Feldman et al. | |
| 2004/0066506 A1 | 4/2004 | Elichai et al. | |
| 2004/0179727 A1 * | 9/2004 | Takeuchi | 382/145 |
| 2004/0254669 A1 * | 12/2004 | Badar | 700/121 |
| 2006/0103838 A1 * | 5/2006 | Richter et al. | 356/237.5 |

* cited by examiner

*Primary Examiner*—Tarifur Chowdhury
*Assistant Examiner*—Tara S Pajoohi
(74) *Attorney, Agent, or Firm*—SNR Denton US LLP

(57) ABSTRACT

A method for inspecting a plurality of dies, that are typically disposed on a surface of a semiconducting wafer. Each of the dies includes respective functional features within the die. The method consists of identifying within a first die a first multiplicity of the functional features having respective characteristics, and measuring respective first locations of the first multiplicity with respect to an origin of the first die. Within a group of second dies a second multiplicity of the functional features having the respective characteristics is identified, respective second locations of the second multiplicity are measured. The second locations are compared to the first locations to determine a location of an origin of the group of the second dies.

12 Claims, 9 Drawing Sheets

METHODS AND APPARATUS FOR INSPECTING A PLURALITY OF DIES

FIELD OF THE INVENTION

The present invention relates generally to methods of process and diagnostics for wafer fabrication, and specifically to accurate methods for inspecting the wafer.

BACKGROUND

In a wafer fabrication facility, optical scanning is one of the recognized methods for inspecting the wafer. The scanning irradiates a specific region of the wafer, for instance in a die or cell on the wafer, and measures one or more parameters of the returning radiation. The measured parameters may be compared with other respective, assumed "standard" parameters, typically in a cell-cell or die-die comparison, or in a comparison against previously determined values, to determine if the irradiated region is within specification.

In all cases, the comparison relies on knowledge of the locations both of the region being inspected, as well as the region from which the standardized parameters have been taken.

Two trends in wafer fabrication increase the difficulty of locating a specific region within a wafer. A first trend is the increase in overall wafer size; a second trend is the reduction in size of elements within the wafer. Wafer sizes have increased from initial diameters of 100 mm to the 300 mm diameters typical today. Rule sizes, of elements on the wafer, have decreased from initial values of more than 1 micron to 40 nm. Wafer sizes are set to increase, and rule sizes continue to decrease.

The prior art has a number of approaches which claim to improve the process of locating regions.

U.S. Patent Application 20040066506 to Elichai et al. whose disclosure is incorporated herein by reference, describes a system for compensating for inaccuracies in an optical scanner used in a surface inspection system. A surface of an article is scanned along a scanning axis and a scanning axis signal is output at predetermined distances along this axis. A jitter signal is output whenever the scanner deviates from the scanning axis, and is used to calculate the amount of deviation.

U.S. Pat. No. 5,825,482 to Nikoonahad, et al., whose disclosure is incorporated herein by reference, describes a system to correct for misregistration errors. A reference vector of data samples is obtained by averaging adjacent data sample vectors. A comparison of the data samples in a current vector being processed to data samples that may be offset from the current vector along the direction of the current vector enables the detection and correction of misregistration errors.

SUMMARY OF THE INVENTION

In embodiments of the present invention, a central processor operates inspection apparatus used to inspect the surface of a wafer. The wafer has a plurality of dies on the surface, and each die comprises functional features, such as conducting, insulating, or semi-conducting elements, within the die. One of the dies, typically centrally disposed on the wafer, is selected as a reference die. The processor scans the reference die and uses characteristic signals from scanned elements of the die to identify reference functional features that are to be used in scanning other dies on the wafer. The processor calculates locations of the reference functional features, herein termed reference locations, relative to an origin of measurement of the die.

The processor scans a group of other dies on the wafer, and from the signals generated by the scan identifies reference functional features in the group as those having the characteristic signals determined for the reference die. The processor measures locations of the identified features in the group, herein termed group locations. The processor compares the group locations with the reference locations, and from the comparisons determines an origin of measurement for the group. Determining the origin of the group of dies by comparing measured locations of features within the group with measured locations of the reference die is a fast method for accurately determining the origin of the group. Furthermore, the processor is able to inspect the dies of the group for regions of interest, for example by a die-to-die or cell-cell comparison, using the signals generated by the scan of the group.

In one embodiment, the dies are rectangular, and only a rectangular reference portion of the reference die is scanned to determine the reference functional features. The portion has a geometric relationship with the reference die, for example, the portion and the die have one overlapping congruent edge. The group of dies is in the form of a rectangular column of the dies, and only a rectangular portion of the column, having the same geometric relationship to the column as the portion to the reference die, is scanned to determine the reference functional features in the group, and the corresponding group locations. The origin of the group that the processor determines corresponds to the origin of the column. Accurately determining the origin of the column facilitates the identification of regions of interest that are found as the processor inspects the column of dies.

In some embodiments, multiple scans of a portion of the reference die, and overlapping scans of the remainder of the die, are used to determine locations of reference functional features over the whole die. In these embodiments, signals derived from scans of the remaining dies may be used to determine origins of columns, or sections of columns, as well as to identify regions of interest of the dies.

The present invention will be more fully understood from the following detailed description of the embodiments thereof, taken together with the drawings in which:

DETAILED DESCRIPTION

Figure 1:
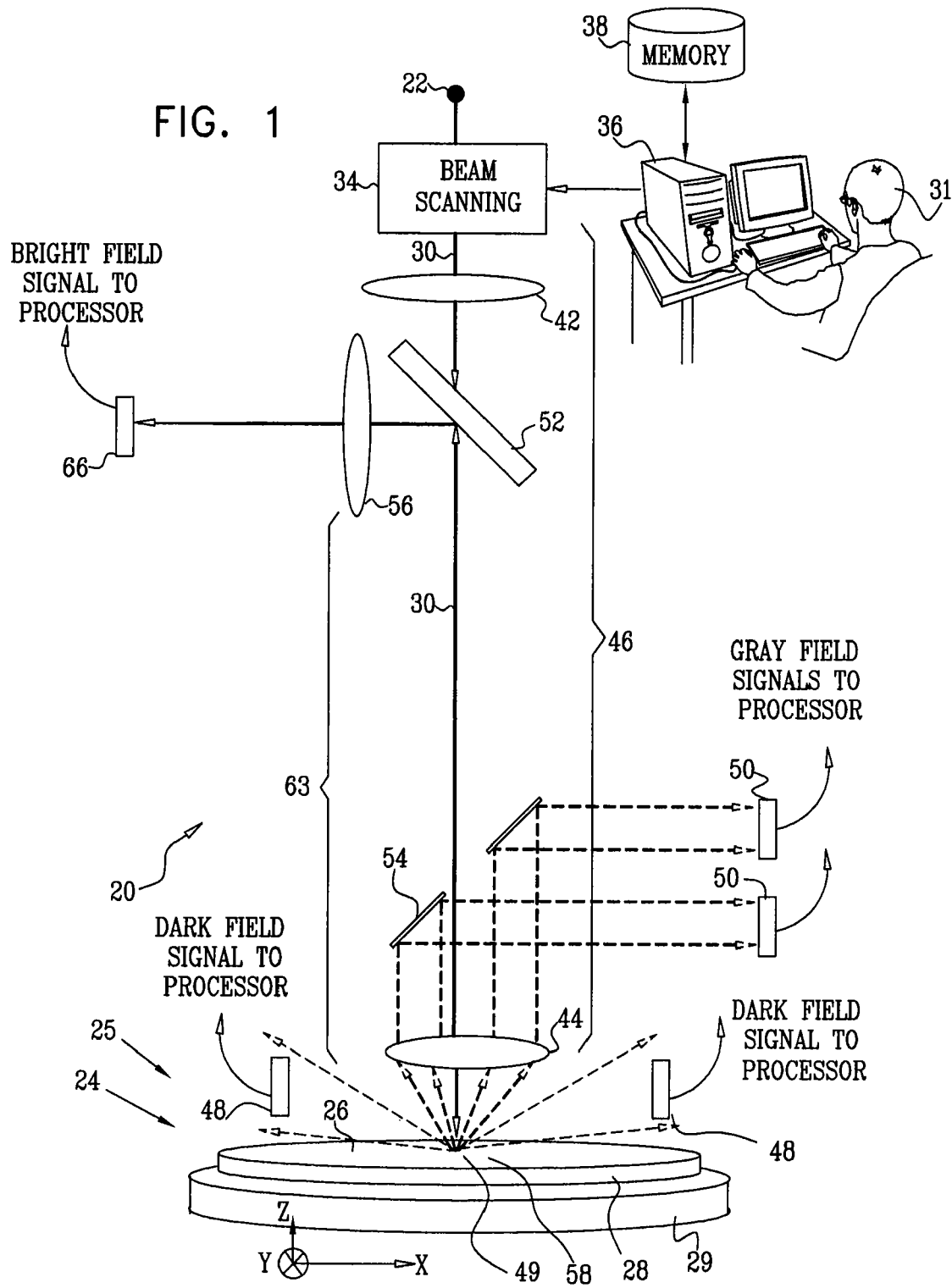
FIG. 1 is a schematic diagram of a surface inspection apparatus, according to an embodiment of the present invention.

Reference is now made to FIG. 1, which is a schematic diagram of a surface inspection apparatus 20, according to an embodiment of the present invention. Apparatus 20 comprises a source 22 of radiation which generates a beam 30 that is used to irradiate a surface 26. Herein, by way of example, surface 26 is assumed to comprise the surface of a wafer 28, but it will be appreciated that embodiments of the present invention may be used for irradiation and/or inspection of substantially any surface. Wafer 28 has a multiplicity of substantially similar dies 24 formed on its surface. There are a multiplicity of functional features 25, such as memory cells, logic cells, or groups or components thereof, within each die. In the following description, specific dies 24 are referred to by adding a letter suffix to the identifying numeral, for example die 24A. Source 22 is typically a laser, although any other suitable source of radiation, such as an ultra-violet (UV) or deep UV lamp, may be used to generate beam 30. An operator 31 may control apparatus 20, or alternatively the apparatus may be configured to operate substantially automatically. The structure of the dies, and their relative positioning, is described in more detail below with reference to FIGS. 2, 3, and 4.

For clarity in the following description, surface 26 is assumed to define an x-y plane, with the x-axis lying in the plane of the paper, and the y-axis going into the paper. A z-axis is normal to the x-y plane, as shown in FIG. 1. The description also uses, for clarity, positional terms with respect to the figures such as left side and lower section of the wafer. The axes and the positional terms are arbitrary, and are not to be construed as limiting the scope of the present invention.

Beam 30 enters a beam scanning module 34 which scans the beam in an x-direction, typically using rotating mirrors and/or acousto-optic deflectors. Elements for performing the functions of module 34 are well known in the art. U.S. Pat. Nos. 6,853,475 and 6,809,808 to Feldman et al, describe examples of such elements. Module 34 is controlled by a processor 36, which also operates other elements of apparatus 20. Processor 36 is coupled to a memory 38, wherein are stored instructions for operation of the apparatus.

Module 34 is part of a set of projection optics elements 46, which also include other elements, indicated schematically in FIG. 1 by a relay lens 42 and an objective lens 44. Projection optics 46 function to project and focus radiation from beam 30 onto a spot 49 on surface 26. Optics 46 also include a beamsplitter 52, which allows transmission of beam 30 to surface 26.

Typically, spot 49 covers a multiplicity of pixels 58 of surface 26, the number of pixels being a function of several factors including the wavelength of source 22, the numerical aperture of the optics, and the size of the pixels. The size of a pixel is typically selected according to the design rule used in forming dies 24 on the surface. For example, each pixel 58 may be a square of side 160 nm.

Wafer 28 is mounted on a motion stage 29 which is controlled by processor 36. Stage 29 rotates and translates the wafer, using independent x-, y-, and z-translation stages, as well as one or more rotation stages. Processor 36 controls the movement of the motion stages, as well as the scanning performed by module 34, so that substantially any part of surface 26 may be irradiated by beam 30. The particular motions generated by module 34 and stage 29 are described in more detail below.

Returning radiation from spot 49 is typically of three forms: bright field radiation, comprising radiation which is substantially specularly reflected from surface 26, dark field radiation, which is typically radiation which is scattered from surface 26 at relatively large angles, of the order of 30° or more, to the path of the specular reflected radiation, and gray field radiation, which is scattered from surface 26 at angles between the path of the specular reflected radiation and the dark field radiation. Generally, in inspecting surface 26, all three forms of returning radiation are measured.

In apparatus 20 beam 30 is arranged to be incident substantially normally on surface 26, although the apparatus could be set to operate at non-normal angles of incidence. A mirror 54 has a hole at its center to allow free passage of beam 30, as well as returning specular radiation from spot 49. Specular radiation from spot 49 traverses objective 44, and is reflected by beamsplitter 52 via a lens 56 to a bright field detector 66. Objective 44, beamsplitter 52, and lens 56 are part of a set of receiving optics 63.

Mirror 54 reflects gray field radiation from spot 49 to gray field detectors 50. Dark field radiation is measured by detectors 48. For clarity, in FIG. 1 only two gray field detectors and two dark field detectors are shown, but it will be understood that there are typically more than two of each type in apparatus 20. Typically, the dark field and gray field detectors are distributed approximately symmetrically about beam 30. By way of example, apparatus 20 is assumed to comprise a total of 15 bright field, gray field, and dark field detectors.

Returning radiation from spot 49 impinges on each of detectors, 66, 50, and 48, and the detectors in turn generate respective signal levels for pixels 58 according to their received radiation intensity. The specific signal levels for each detector are characteristic of the functional features of the pixel being irradiated, as well as of the intensity of beam 30. Thus, a matrix of up to 15 different detector levels may be associated with each pixel 58, element values of the matrix for a particular pixel being dependent on the functional features of the pixel. For example, a pixel which comprises a conducting metallic strip, such as may be used for a bus of a circuit, typically has a significantly different matrix compared to the matrix associated with an insulator.

Typically, embodiments of the present invention inspect surface 26 using comparisons of detector levels. The comparisons may be on a pixel to pixel basis, wherein a first pixel matrix of up to 15 detector levels may be compared with a second pixel matrix with the same number of levels. Alternatively, the comparisons may be on a group-of-pixel to group-of-pixel basis, using one detector level. In this case matrices of a given detector level, for example the bright field detector level, are compared, and the number of elements in the matrices correspond to the number of pixels in the group. Further alternatively, the comparisons may be on a group-of-pixel to group-of-pixel basis, using more than one detector level per pixel, in which case the number of elements in the matrices is a product of the number of detector levels and the number of pixels in the group. The matrices that are compared are also referred to herein as signal matrices. Yet further alternatively, the comparisons may be on a basis of a group-of-pixels of a given detector, e.g., a bright field detector, to a group-of-pixels of the same detector, where the number of elements in the matrix is the numbers of pixels in the group, e.g., for a matrix of 3 rows and 3 columns there are 9 elements.

Typically, processor 36 inspects surface 26 as quickly as possible. The processor typically performs the inspection by irradiating consecutive rectangular regions of the surface, each rectangular region being inspected by scanning beam 30 in the x-direction while translating surface 26 in the y-direction. The rectangular region swept out by the scanned beam is also herein termed a slice. Slices and their dimensions are described in more detail with respect to FIG. 3 below. To reduce the time spent on inspection, processor 36 may set the rate of scanning of beam 30 and the rate of translation of surface 26 as high as possible, while providing an acceptable signal to noise level at each of detectors 48, 50, and 66. Typically, rates of scanning across surface 26 are in the range 80-260 mm/s.

By way of example, the description herein assumes that apparatus 20 uses one beam 30 which irradiates a single spot 49 of surface 26. Methods are known in the art to irradiate multiple spots of surface 26 substantially simultaneously, for example, by multiplexing beam 30 into a multiplicity of beams, and/or by using multiple radiation sources, and/or by broadening the focus of the beam. Those having ordinary skill in the art will be able to adapt the description herein, mutatis mutandis, for systems irradiating multiple spots substantially simultaneously.

Figure 2:
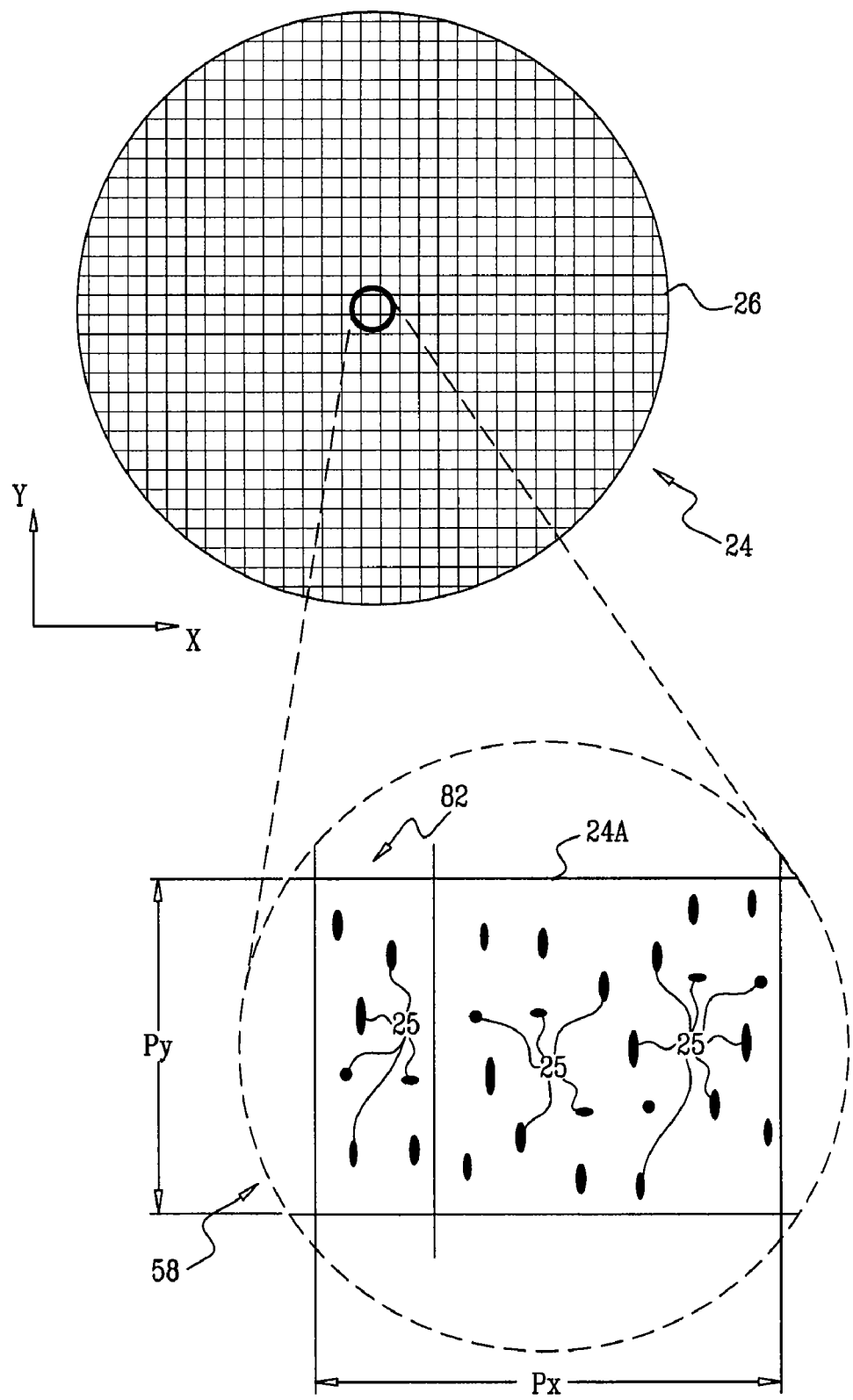
FIG. 2 is a schematic diagram of an aspect of a surface, according to an embodiment of the present invention.
Figure 3:
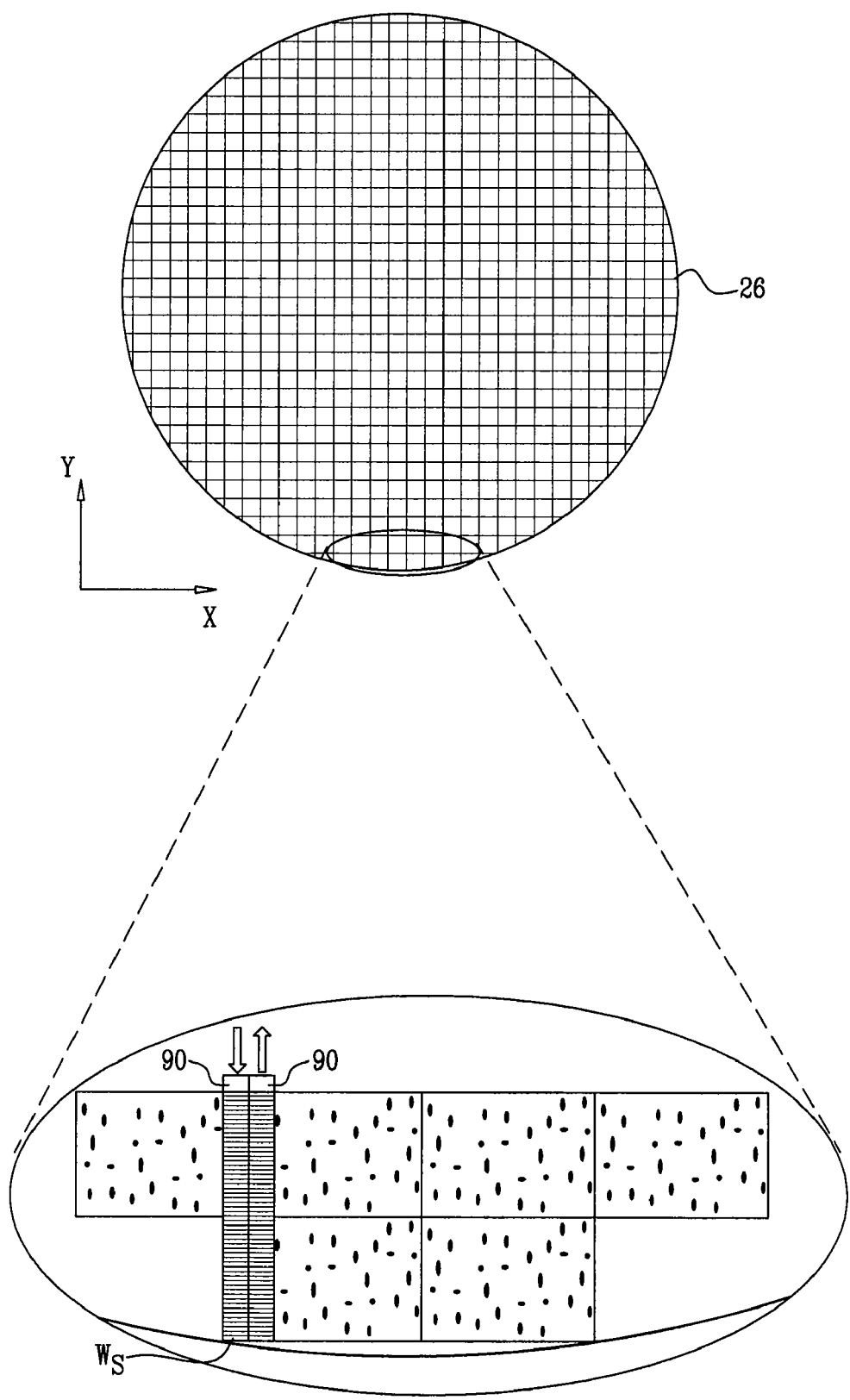
FIG. 3 is a schematic diagram of another aspect of the surface, according to an embodiment of the present invention.
Figure 4:
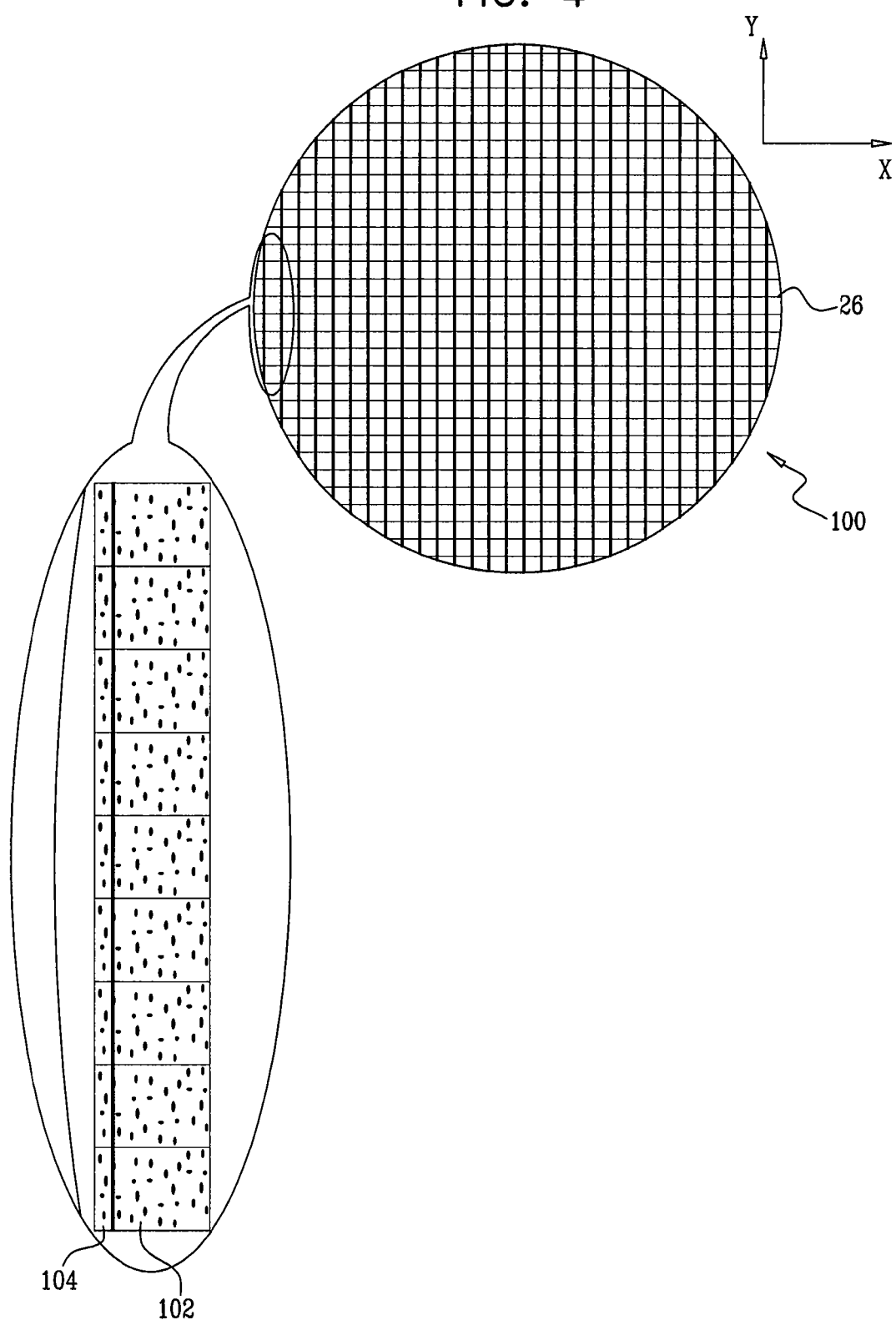
FIG. 4 is a schematic diagram of a further aspect of the surface, according to an embodiment of the present invention.

FIGS. 2, 3, and 4 are schematic diagrams of different aspects of surface 26, according to an embodiment of the present invention. Dies 24 are assumed to be formed on surface 26 in a repeating grid pattern, herein assumed to be a rectangular grid pattern. A generally central die 24A is shown enlarged in FIG. 2. The rectangular grid of dies is formed to have respective theoretical spatial periodicities, parallel to the x- and y-axes, represented by $p_x$ and $p_y$. Thus, each die, including spacing between the dies, is a rectangle having dimensions $p_x$ by $p_y$, where $p_x$ and $p_y$ are numbers of pixels in the x and y directions respectively. In inspecting dies 24, apparatus 20 typically applies one of the signal matrix comparison techniques described above, by comparing signal matrices formed from one or more corresponding pixels of different dies (die-to-die comparison), comparing signal matrices of one or more pixels of a die with a stored signal matrix, for example in a database, and/or comparing matrices generated by cells, such as memory cells, within a die. All such comparisons rely on accurate knowledge of the locations of the pixels being compared. Embodiments of the present invention provide a method for ensuring that locations of pixels being inspected are accurately known.

Each die 24 comprises a multiplicity of different functional features 25 which, because they are contained within a die, each have the same theoretical spatial periodicity as the dies. Each feature 25 comprises one or more pixels and has respective characteristics, such as acting as a transistor, memory cell, resistor, conductor, insulator, and/or capacitor, or acting as a part thereof. The characteristics of each feature also include, inter alia, effects of the feature on incident radiation. As is described in more detail below with respect to FIG. 6, embodiments of the present invention use some of features 25 as registration features. The use of a section 82 of die 24A is described in more detail below, with reference to FIG. 6.

FIG. 3 schematically shows a lower section of surface 26. Dies 24 are inspected by translating wafer 28 in a y-direction, while module 34 scans beam 30 in an x-direction, irradiating columns of the dies in slices. Columns are described below with respect to FIG. 4. A width $w_s$ of a slice 90 is configured so that respective portions of dies 24 are scanned during y-translation. By way of example, FIG. 3 shows parts of two slices 90, one slice being scanned with a positive y-translation, the other with a negative y-translation. Both slices 90 are shown traversing the lower two dies 24 of the section. The two slices 90 terminate, in the example described herein, at the upper edge of an uppermost die 24 (for clarity not shown in FIG. 3) of a column of dies on surface 26. In one embodiment of the present invention, $w_s$ is configured to be $$\frac{1}{20}.$$

$p_x$, so that twenty contiguous slices 90 cover a complete die and/or a complete column. In some embodiments, the slices may overlap in an x-direction, in which case more than twenty slices are used to inspect a complete die and/or a complete column.

FIG. 4 shows dies 24 grouped in columns 100, and an enlargement in FIG. 4 shows a left-most column 102 of the dies, comprising, by way of example, nine dies. Column 102 thus has an x-dimension $p_x$, and a y-dimension $9p_y$. A rectangular section 104 of column 102 is described in more detail below with reference to FIG. 6. Other columns 100 have heights according to their x position on surface 26. Typically, inspection of a given column 100 of dies 24 is performed by scanning slices having the same height as the column over the column of dies.

Figure 5:
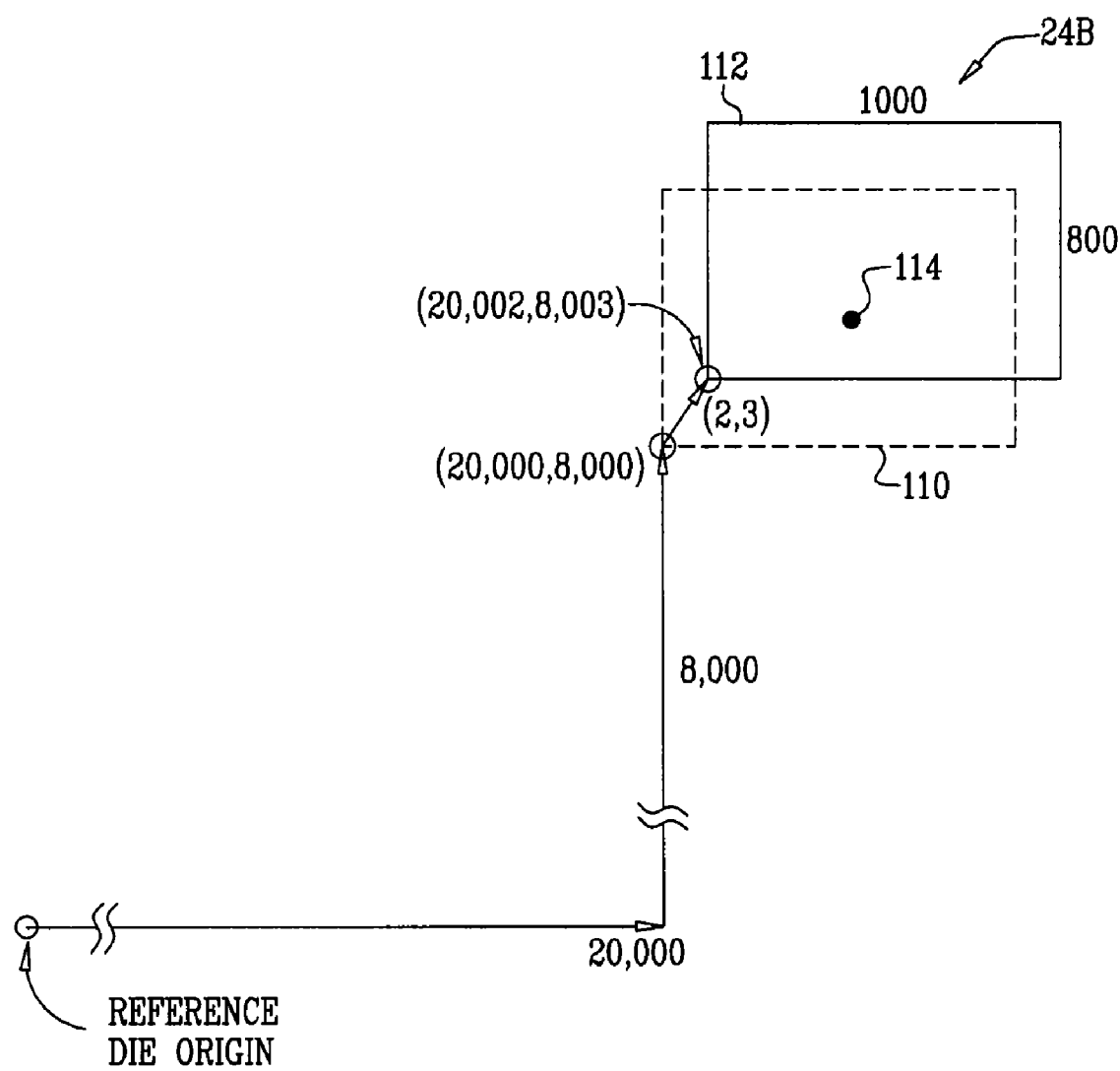
FIG. 5 is a schematic diagram showing a nominal location and an actual location of a die on a surface, according to an embodiment of the present invention.

FIG. 5 is a schematic diagram showing a nominal location 110, and an actual location 112, of a die 24B on surface 26, according to an embodiment of the present invention. By way of example, dies 24 have dimensions of $p_x=1000$ and $p_y=800$, and the actual location of die 24B is displaced from the die's nominal location by a displacement vector (x,y)=(2,3). In the x-direction, die 24B is the 21$^{st}$ die from a reference die 24 (not shown in FIG. 5), in the y-direction die 24B is the 11$^{th}$ die from the reference die. Thus, a nominal location of the origin of die 24B is (20,000, 8,000). Because of the displacement of the actual die, the actual location of the origin of die 24B is (20,002, 8003). In general:

$$(x_A, y_A) = (x_N, y_N) + (x_D, y_D) \tag{1}$$

where $(x_A, y_A)$ is an actual vector of a location in die, such as the origin of the die;

$(x_N, y_N)$ is the nominal vector of the location, and $(x_D, y_D)$ is the displacement vector from the nominal die to the actual die.

The displacement of the actual die location relative to the nominal die location causes a corresponding difference in vectors of a region within die 24B. Thus, if spot 49 is positioned by processor 36 at a location (20,500, 8,400), corresponding to a nominal center 114 of die 24B, a nominal local vector for the spot within die 24B, measured relative to the nominal origin of the die at (0, 0), is (500, 400). However, expression (1) gives the actual origin as (2, 3). Thus, the spot that is irradiated by beam 30 has an actual local vector (498, 397). It will be understood that the actual local vector, rather than the nominal local vector, describes the region irradiated by beam 30. Thus, if inspection of surface 26 indicates the existence of a region of interest, such as a possible defect, the actual local vector is compared with the theoretical "map" of the die in order to determine the element of the die that is of interest.

Figure 6:
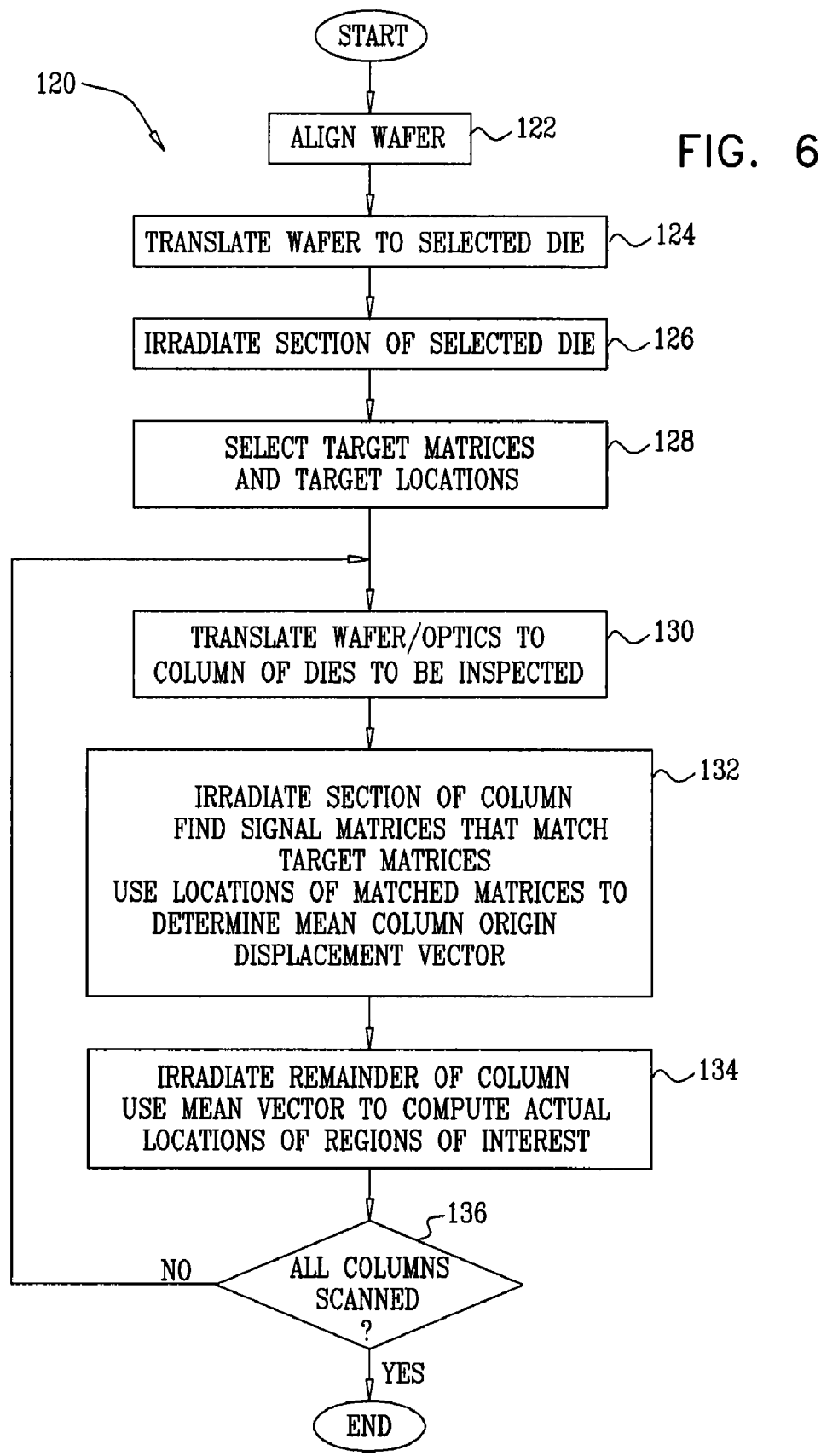
FIG. 6 is a flowchart showing steps performed by the apparatus of FIG. 1, according to an embodiment of the present invention.

FIG. 6 is a flowchart 120 showing steps performed by apparatus 20 to determine actual origins of sections of surface 26, and to inspect the surface, according to an embodiment of the present invention.

In a first step 122, processor 36 aligns wafer 28 so that columns 100 (FIG. 4) are parallel to the y-direction of the y-translation stage of stage 29. Processor 36 performs the alignment using the one or more rotation stages of motion stage 29.

In a second step 124, the processor translates wafer 28 so that a given die 24, typically a relatively central die such as die 24A exemplified in FIG. 2, may be irradiated by beam 30. The selected die is herein referred to as reference die 24A. Processor 36 may perform the translation automatically, using theoretical dimensions of wafer 28 and positions of dies 24 on surface 26. Alternatively or additionally, the processor may irradiate surface 26 with beam 30, and use signal matrix values, such as those generated by edges of dies 24, to determine that beam 30 is correctly positioned. Further alternatively or additionally, operator 31 may provide input to the processor, such as specific coordinates, so that the translation is performed at least partially manually.

In a third step 126, processor 36 irradiates section 82 (FIG. 2) of die 24A. Section 82 is set to be a rectangle having the same orientation and height as die 24A. Processor 36 sets a distance $d_x$ of the left side of section 82 from the left side of die 24A, and a width $w_x$ of section 82, according to expression (2):

$$w_x \leq p_x$$

$$0 \leq d_x \leq (p_x - w_x) \quad (2)$$

The values of $w_x$ and $d_x$ given in expression (2) determine a geometric relation between section 82 and die 24A. Typically, $d_x=0$ and $w_x<p_x$, so that the section and the die have one overlapping congruent edge.

Processor 36 typically irradiates section 82 by scanning beam 30 in an x-direction, while translating the wafer in a y-direction, for example by scanning two slices, substantially as described above with reference to FIG. 3, the slices having heights equal to the die height. In an embodiment of the present invention, each of the two slices is scanned in a positive and in a negative y-direction, and the results of the scans, described below, are averaged. Alternatively, any other suitable method may be used to irradiate section 82. In some embodiments the irradiated section includes the lower left corner of die 24A. During irradiation of the section, processor 36 stores matrices of detector levels of the scanned pixels, and the corresponding locations of the pixels, in memory 38. The stored matrices are herein termed calibration matrices. The locations are in the form of ordered (x, y) pairs, the x and y values typically being measured in pixel and/or sub-pixel numbers, and are set directly by processor 36.

Processor 36 selects one of the stored locations to be considered as the origin of measurements for the die. Typically, the selected location is the lower left corner of die 24A. However, the processor may select any other of the stored locations as the origin of measurements.

As described in the following step, some of the calibration matrices derived during step 126 are used as references. To improve the accuracy of the calibration matrices, the rate of x-scanning of beam 30, and/or the rate of y-translation of surface 26, may be reduced compared to the rates given above in reference to FIG. 1. A typical reduction is by a factor of 10, so that scanning rates may be in a range 8-26 mm/s.

The inventors have found that an area of section 82 is advantageously approximately 0.5-10% of the area of die 24A. However, those with ordinary skill in the art will be able to determine other areas for section 82, as well as other rates for irradiating the section, so as to generate calibration matrices of sufficient accuracy, without undue experimentation.

In a fourth step 128, the processor automatically selects matrices and locations, or sets of matrices and respective sets of locations, from amongst the stored calibration matrices and respective stored locations. The selected matrices are characteristic of the respective features generating the matrices. The selected matrices and their locations are used as fiducial references, and are also herein termed target matrices and target locations.

Embodiments of the present invention provide a number of different methods by which processor 36 selects the target matrices and locations. In one embodiment of the invention, operator 31 stores values of matrices and respective locations to be used as references in memory 38 prior to implementing flowchart 120. Processor 36 compares the calibration matrices determined in step 126 with the matrices stored by the operator in memory 38 in order to select the target matrices and corresponding target locations. Alternatively or additionally, prior to implementing flowchart 120, operator 31 provides processor 36 with instructions as to how to select the target matrices. The instructions typically comprise searching within the calibration matrices for predetermined sets of the calibration matrices and/or for ranges of values of elements of the calibration matrices. Further alternatively or additionally, prior to implementing flowchart 120, operator 31 provides locations to be used as target locations to processor 36, and the processor uses the calibration matrices of the provided locations as target matrices. Yet further alternatively or additionally, processor 36 may select the target locations and/or target matrices from a database of locations and/or matrices. In some embodiments, processor 36 selects the target matrices so that the corresponding target locations are distributed uniformly over section 82. By way of example, it is assumed that processor 36 selects $N_{ref}$ target locations.

In a fifth step 130, processor 36 translates the wafer so that spot 49 aligns with a column having dies that are to be inspected. Typically, when step 130 is first implemented, the column selected is close to or at the edge of wafer 28. By way of example, at the first implementation of step 130, spot 49 is hereinbelow assumed to align with left-most column 102 (FIG. 4).

In a sixth step 132, the processor irradiates rectangular section 104. Section 104 is configured to have the same height as column 102, and the same width as section 82, i.e., $w_x$. The processor sets a geometric relationship between section 104 and column 102 to be the same as that between section 82 and die 24A, so that the relationship given by expression (2) applies to section 104 and column 102. The method of irradiation that the processor uses is typically similar to the method used for irradiation of reference die 24A. Thus, if two slices are used to irradiate section 82, two slices are used to irradiate section 104. In some embodiments, rather than irradiating each slice of section 104 in both y-directions, each slice is only irradiated in one direction.

As the irradiation proceeds, processor 36 compares the signal matrices generated with the target matrices, in order to find locations in section 104 that match the target locations of die 24A. The locations so found in section 104 are also termed target locations. The comparison is facilitated since the processor sets the actual location on surface 26 that is irradiated. As described above with reference to FIG. 5, any given vector location set by the processor corresponds to a nominal vector location within a die. Typically, in performing its comparisons, the processor only uses signal matrices of target locations within a relatively small area around the location being checked, such as within a circle having a radius of approximately 8-16 pixels centered on the location, or within a rectangle of side up to 32 pixels centered on the location. In one embodiment, the displacement from the nominal location is assumed to be no more than about 5 pixels. Thus, the number of comparisons checked for each location in section 104 is relatively small, so that processor 36 is able to make the comparisons in real time.

For each given target location in section 104, the processor uses the values of $(x_A,y_A)$, $(x_N,y_N)$, and expression (1), to determine vector $(x_D,y_D)$ for the given target location. It will be appreciated that the values of $(x_A,y_A)$ are set by processor 36, and the values of $(x_N,y_N)$ are known from the theoretical layout of dies 24 on surface 26. As the irradiation of the section proceeds, the processor calculates respective values for $(x_D,y_D)$ for each target location in the section, and averages the values to generate a mean column 102 displacement vector $\overline{(x_D,y_D)}$.

Mean vector $\overline{(x_D,y_D)}$ describes the displacement of the origin of column 102 from its nominal location. Herein the notation $\overline{(x_D,y_D)}_C$ represents a mean vector describing the displacement of the origin of a column C from its nominal location.

During the irradiation of section 104, processor 36 may also perform die-to-die and/or cell-to-cell comparisons, to determine regions of interest, such as defects, in section 104. The location of any such region of interest is calculated using expression (1), using the value of mean vector $\overline{(x_D,y_D)}$ determined as described above. Alternatively or additionally, during irradiation of section 104, processor 36 may perform a comparison with a database of signal matrices to determine regions of interest. Such a comparison may advantageously be made by storing signal matrices and corresponding locations for section 104. After mean vector $\overline{(x_D,y_D)}$ has been determined, its value is applied to the scanned locations to determine adjusted actual locations, and values of the signal matrices for the actual locations are compared with the database.

In a seventh step 134, processor 36 scans the remainder of column 102, typically by sequentially scanning slices of the column substantially similar to slices 90, and continues to perform the die-to-die and/or cell-to-cell and/or database comparisons described above. For each region of interest determined by the processor, it uses expression (1), applying mean vector $\overline{(x_D,y_D)}$, to compute the actual location of regions of interest found.

In an eighth step 136, performed once column 102 has been completely scanned, processor 36 determines if there are remaining columns on surface 26 to be scanned. If there are none, flowchart 120 ends.

If there are remaining columns, processor 36 repeats steps 130, 132, and 134, typically by moving to a column adjacent to a column that has just been scanned. Since there is typically relatively little change in values between mean vectors $\overline{(x_D,y_D)}_C$ and $\overline{(x_D,y_D)}_{(C+1)}$, processor 36 may advantageously use the value found for the mean vector $\overline{(x_D,y_D)}_C$ as a predictor for $\overline{(x_D,y_D)}_{(C+1)}$, enabling the processor to narrow the numbers of reference features that need to be compared before matching reference features are found.

Figure 7:
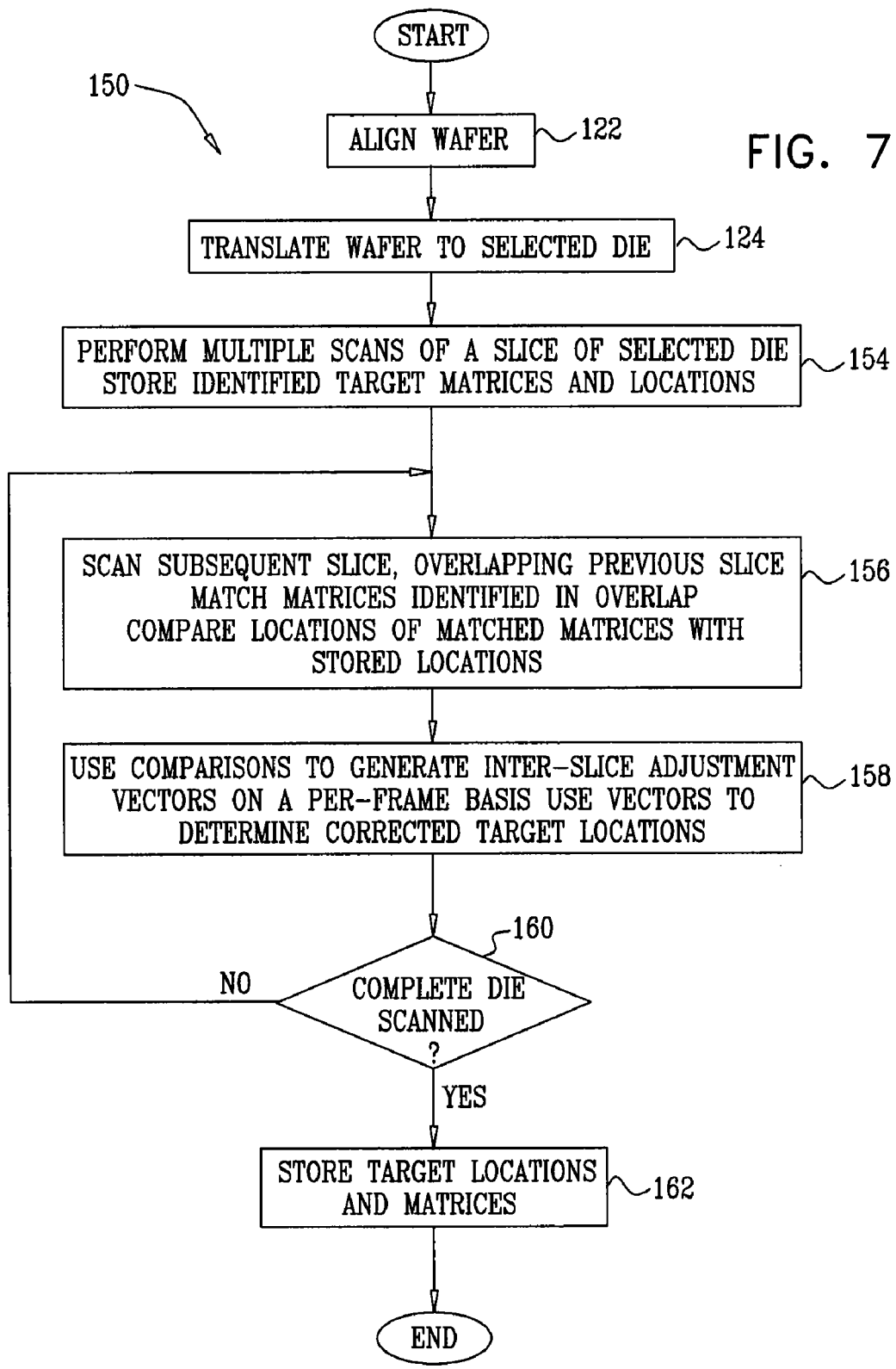
FIG. 7 is a flowchart showing steps performed by the apparatus of FIG. 1, according to an alternative embodiment of the present invention.
Figure 8:
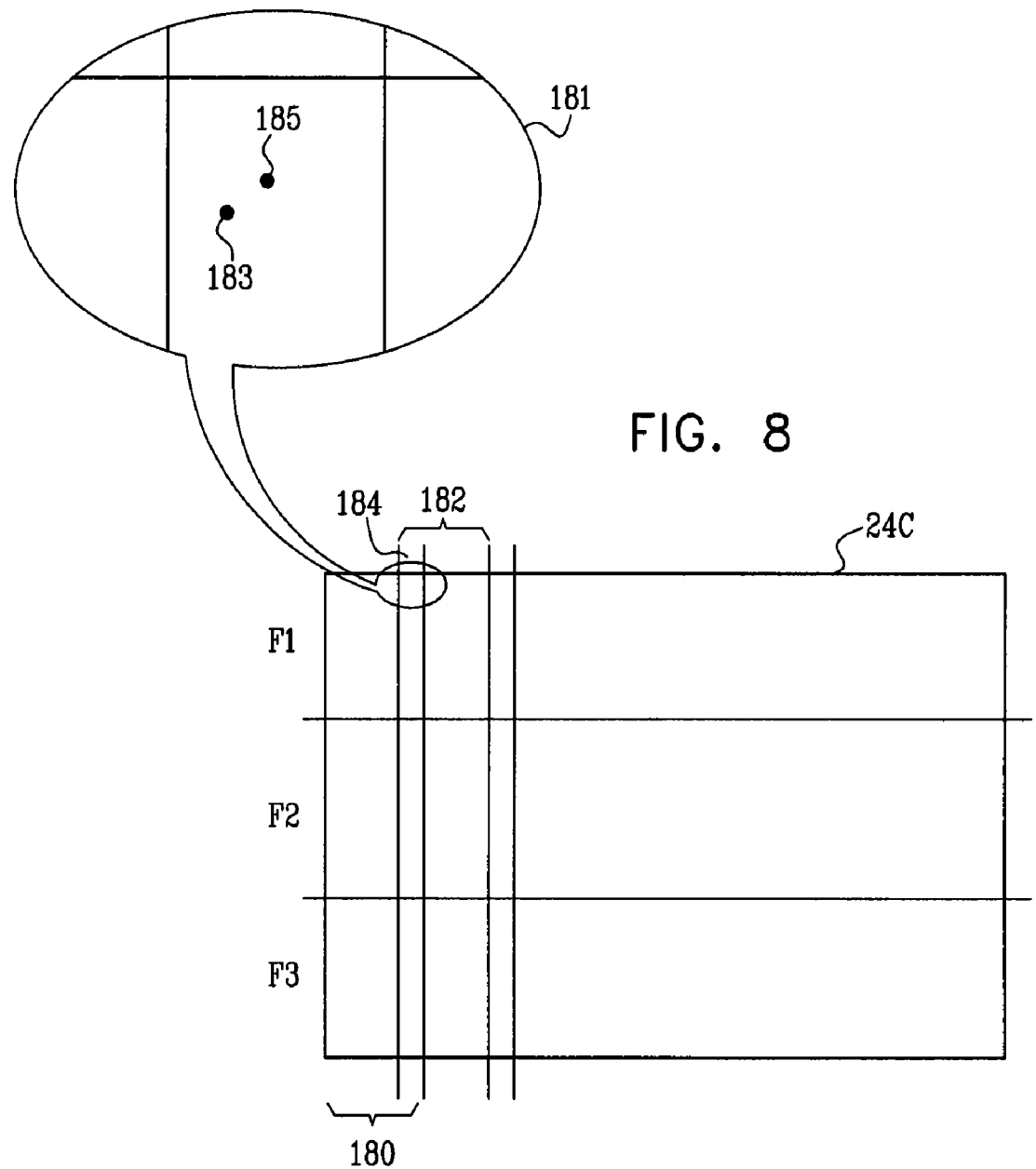
FIG. 8 is a schematic diagram of a die illustrating actions performed in the flowchart of FIG. 7, according to an embodiment of the present invention.

FIG. 7 is a flowchart 150 showing steps performed by apparatus 20 to determine target locations of a reference die, according to an alternative embodiment of the present invention. FIG. 8 is a schematic diagram of a die 24C illustrating actions performed in flowchart 150, according to an embodiment of the present invention. Flowchart 150 uses some steps which are generally similar in implementation to those of flowchart 120 (FIG. 6), and such steps are indicated by the same reference numerals in both flowcharts. Flowchart 150 is typically performed in a calibration phase of inspection of wafers such as wafer 28.

Steps 122 and 124 are described above with reference to FIG. 5. The located die is herein termed die 24C (FIG. 8). Each slice of die 24C is assumed to be divided into a number of horizontal frames, each frame having the same width as its slice. By way of example, the following description assumes there are three frames F1, F2, and F3 for each slice.

In a step 154, processor 36 performs multiple scans, for example ten scans, of a first slice 180 of die 24C, identifying targets and averaging locations of the targets, substantially as described above for steps 126 and 128. The processor stores identified target matrices and the corresponding averaged values of the target locations in memory 38. In addition, processor 36 assigns each stored target to frame F1, F2, or F3 according to the location of the target. By performing the multiple scans, the error of each target location is reduced.

In a step 156, processor 36 scans a second slice 182 of die 24C (FIG. 8). The processor configures slice 182 to partially overlap slice 180, in a region 184. On a per-frame basis, the processor identifies target matrices in slice 182 substantially as described for step 128, and generates temporary location values for the matrices. The processor matches the matrix identified for each frame in region 184 of slice 182 with the same matrices in the corresponding frame of slice 180 already identified in step 154, and compares the temporary location values of the matched matrices with their locations determined in step 154. Matrices are assumed to match with each other if an absolute value of a normalized correlation coefficient, defined below, is greater than or equal to approximately 0.7. An enlargement 181 of overlapping region 184 illustrates the matching with an example location 183 and an example location 185. Location 183 is the location of a target matrix as determined by processor 36 for slice 180. Location 185 is the temporary location of the matched target matrix for slice 182. After matching the targets in the respective frames, the corresponding frames of the overlapping slices, 180 and 182, can be advantageously aligned.

The normalized correlation coefficient, C, between two matrices A(n,m) and B(n,m), where A and B are matrices having n rows and m columns, is given by the expression (3):

$$C = \frac{\langle A, B \rangle}{\sqrt{\langle A, A \rangle} \cdot \sqrt{\langle B, B \rangle}} \quad (3)$$

where $$\langle A, B \rangle = \sum_{i=1}^{n} \sum_{j=1}^{m} A(i,j) \cdot B(i,j)$$

In a step 158, using an expression similar to expression (1) above, the processor uses the comparisons of step 156 to generate inter-slice adjustment vectors that describe the difference between the locations stored in step 154 and the temporary locations found in step 156. The processor generates an inter-slice adjustment vector for each of frames F1, F2, and F3. Processor 36 applies a respective inter-slice adjustment vector to each of the temporary location values determined in step 156, according to the frame that the target is in, to determine corrected location values for the targets determined in the second slice.

Steps 156 and 158 are repeated for the remainder of die 24C, until the complete die has been scanned, as shown in a step 160. In each repetition, processor 36 configures a new slice to overlap the immediately preceding slice, and uses the overlap to generate respective inter-slice adjustment vectors by correlating locations of the same targets found in the overlapping slices. The processor uses the inter-slice adjustment vectors to determine corrected location values for each target of die 24C.

The iterative procedure of steps 156, 158, and 160, sequentially matches target locations to previous target locations in overlapping slices. The procedure provides an efficient, quick, method for locating all the target locations of die 24C with substantially the same accuracy as the accuracy of slice 180.

In a final step 162 of the flowchart, processor 36 stores target matrices and corrected target locations according to frames in memory 38.

Figure 9:
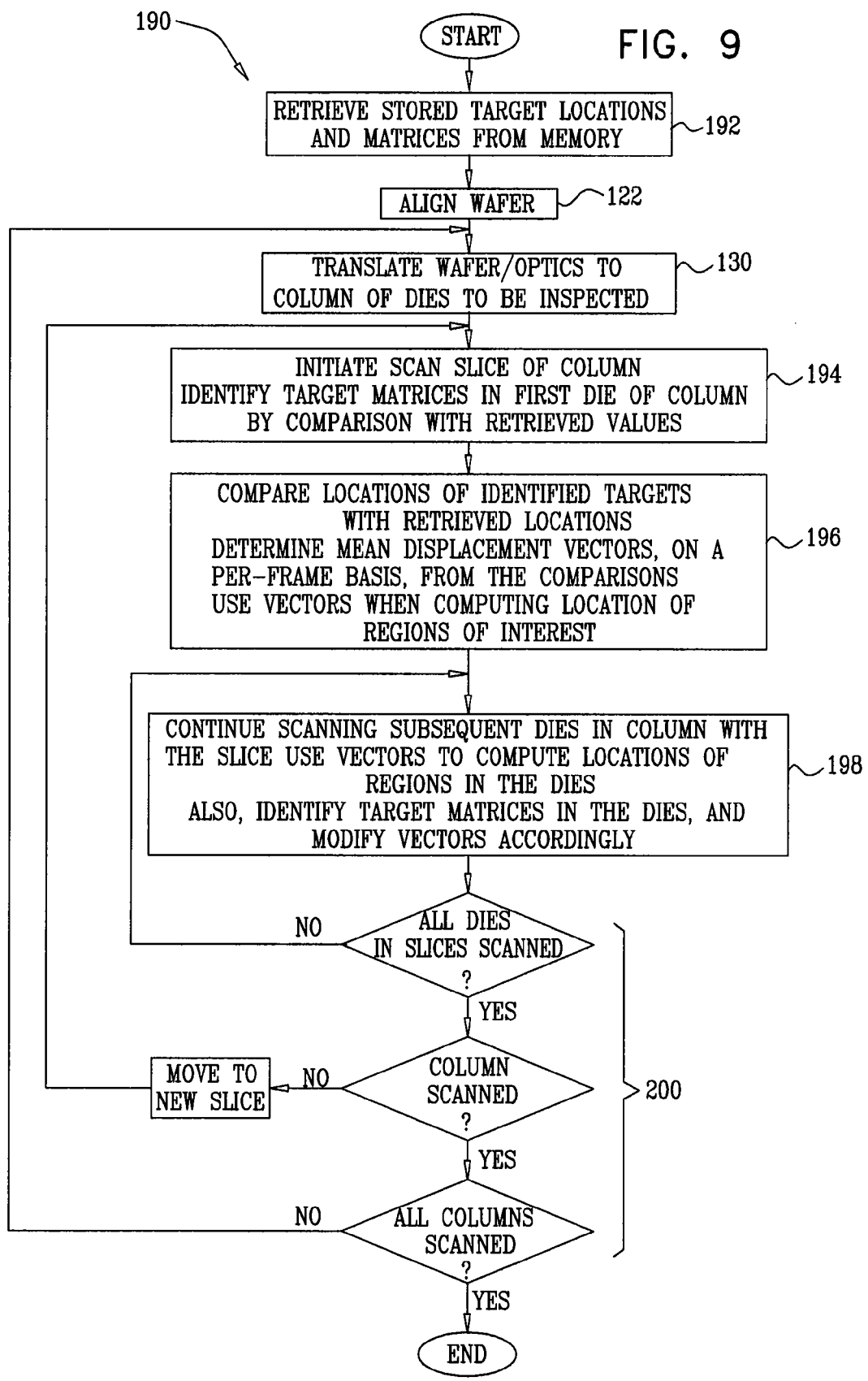
FIG. 9 is a flowchart showing steps performed by the apparatus of FIG. 1 in inspecting a surface, according to an alternative embodiment of the present invention.

FIG. 9 is a flowchart 190 showing steps performed by apparatus 20 in inspecting surface 26, according to an embodiment of the present invention. Flowchart 190 uses some steps which are generally similar in implementation to those of flowchart 120 (FIG. 6), and such steps are indicated by the same reference numerals in both flowcharts. Flowchart 190 is typically performed in a production phase of inspection of wafers such as wafer 28, typically after flowchart 150 has been implemented.

In a step 192, the processor retrieves stored values of target locations and target matrices from memory 38. The stored values may be generated using flowchart 150.

Processor 36 performs steps 122 and 130 substantially as described above for flowchart 120, so as to align a selected column prior to irradiation.

In a step 194, processor 36 initiates a scan of a first slice of the selected column. The processor identifies target matrices in a first die scanned, by comparison with the retrieved values, substantially as described above with reference to step 132.

In a step 196, the processor compares locations of the identified target matrices with the retrieved locations to determine mean displacement vectors for the slice, on a per-frame basis. Frames are described above with reference to FIG. 8. Each mean displacement vector describes the displacement of a frame of the die. Thus, the processor determines three mean displacement vectors for respective frames in the slice. A notation used herein for the vectors is $\overline{(x_D, y_D)}_{SCF}$, where S represents a number of a slice in a column C, and F represents the frame, in the example herein F1, F2, or F3, of the slice.

In computing regions of interest in the first die the processor applies the mean vectors, $\overline{(x_D, y_D)}_{SCF1}$, $\overline{(x_D, y_D)}_{SCF2}$, and $\overline{(x_D, y_D)}_{SCF3}$, to determine the locations of the regions, substantially as described above with reference to expression (1).

In a step 198, the processor continues scanning the slice for subsequent dies in the column. The processor may use the mean vectors determined in the first die to determine the locations of regions of interest in the subsequent dies, for example as a predictor, on a per-frame basis. In addition, during the scanning of the subsequent dies, the processor identifies target matrices and their locations in the dies. As necessary, the processor uses the identified target locations to modify the values of the mean vectors, so that locations are identified on a per-die and a per-frame basis. In other words, for each frame of each die the processor may effectively evaluate an origin, so that there are multiple origins/slice.

In iterative steps 200, the processor repeats steps 194, 196, and 198 for other slices of the column, and continues for all columns of the wafer, until surface 26 has been completely scanned. Flowchart 190 then ends.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for inspecting a plurality of dies, each of the dies including respective functional features therein, the method comprising:
    identifying within a first die a first multiplicity of the functional features having respective characteristics;
    measuring respective first locations of the first multiplicity of the functional features with respect to an origin of the first die;
    identifying within a group of second dies a second multiplicity of the functional features having the respective characteristics;
    measuring respective second locations of the second multiplicity of the functional features; and
    comparing the second locations of the second multiplicity of the functional features to the first locations of the first multiplicity of the functional features to determine a location of an origin of the group of the second dies.

2. The method according to claim 1, wherein the dies have a rectangular form and wherein the group of second dies comprises a rectangular column of dies, and wherein identifying the first multiplicity of the functional features comprises irradiating a first section of the first die having a geometrical relationship to the first die, and wherein identifying the second multiplicity of the functional features comprises irradiation a second section of the column having the geometrical relationship to the column.

3. The method according to claim 2, wherein a ratio of an area of the first section to an area of the first die is less than one and is equal to a ratio of an area of the second section area to an area of the column.

4. The method according to claim 1, wherein identifying the first multiplicity of the functional features comprises:
    irradiating the first die so as to generate first returning radiation therefrom, and forming first signal matrices in response to the first returning radiation;
and wherein identifying the second multiplicity of the functional features comprises:
    irradiating the group of second dies so as to generate second returning radiation therefrom, and forming second signal matrices in response to the second returning radiation; and
    comparing the first signal matrices and the second signal matrices so as to identify the second multiplicity of the functional features having the respective characteristics.

5. The method according to claim 4, further comprising;
    identifying regions of interest in the second group of dies in response to comparisons between the first signal matrices and the second signal matrices; and
    computing respective locations of the regions of interest in response to the origin of the group of the second dies.

6. The method according to claim 1, wherein identifying the first multiplicity of the functional features comprises:
    irradiating a first section of the first die so as to identify a first subset of the first multiplicity of the functional features in response to returning radiation therefrom;
    irradiating a second section of the first die, the second section comprising a region overlapping the first section, so as to identify a second subset of the first multiplicity of the functional features in response to returning radiation therefrom;
and wherein measuring respective first locations of the first multiplicity of the functional features comprises:

comparing, for the overlapping region, the respective first locations of the first subset with the respective first locations of the second subset so as to determine a vector relating positions of the first subset with positions of the second subset; and applying the vector to determine the positions of the second subset with respect to the origin of the first die.

7. Apparatus for inspecting a plurality of dies, each of the dies including respective functional features therein, the apparatus comprising:

a processor, which is adapted to:

identify within a first die a first multiplicity of the functional features having respective characteristics;

measure respective first locations of the first multiplicity with respect to an origin of the first die;

identify within a group of second dies a second multiplicity of the functional features having the respective characteristics;

measure respective second locations of the second multiplicity; and compare the second locations to the first locations to determine a location of an origin of the group of the second dies.

8. The apparatus according to claim 7, wherein the dies have a rectangular form and wherein the group of second dies comprises a rectangular column of dies, the apparatus comprising:

projection optics which are configured to irradiate a first section of the first die, the first section having a geometrical relationship to the first die, and to irradiate a second section of the column, the second section having the geometrical relationship to the column.

9. The apparatus according to claim 8, wherein a ratio of an area of the first section to an area of the first die area is less than one and is equal to a ratio of an area of area of the second section area to an area of the column.

10. The apparatus according to claim 7, and comprising:

projection optics which are adapted to irradiate the first die so as to generate first returning radiation therefrom, and to irradiate the group of second dies so as to generate second returning radiation therefrom; and a detector, which is configured to generate first signal matrices in response to the first returning radiation and to generate second signal matrices in response to the second returning radiation, and wherein the processor is adapted to compare the first signal matrices and the second signal matrices so as to identify the second multiplicity of the functional features having the respective characteristics.

11. The apparatus according to claim 10, wherein the processor is adapted to identify regions of interest in the second group of dies in response to comparisons between the first signal matrices and the second signal matrices, and to compute respective locations of the regions of interest in response to the origin of the group of the second dies.

12. The apparatus according to claim 7, and comprising projection optics which are configured to:

irradiate a first section of the first die and a second section of the first die, the second section comprising a region overlapping the first section, and wherein the processor is adapted to:

identify a first subset of the first multiplicity of the functional features in response to returning radiation from the first section;

identify a second subset of the first multiplicity of the functional features in response to returning radiation from the second section;

compare, for the overlapping region, the respective first locations of the first subset with the respective first locations of the second subset so as to determine a vector relating positions of the first subset with positions of the second subset; and apply the vector to determine the positions of the second subset with respect to the origin of the first die.

* * * * *